US007125679B2

(12) United States Patent
Ashkar

(10) Patent No.: US 7,125,679 B2
(45) Date of Patent: Oct. 24, 2006

(54) METHODS TO SCREEN PEPTIDE LIBRARIES USING MINICELL DISPLAY

(75) Inventor: Samy Ashkar, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 493 days.

(21) Appl. No.: 10/091,724

(22) Filed: Mar. 6, 2002

(65) Prior Publication Data

US 2003/0105310 A1 Jun. 5, 2003

Related U.S. Application Data

(60) Provisional application No. 60/306,946, filed on Jul. 20, 2001, provisional application No. 60/274,039, filed on Mar. 7, 2001.

(51) Int. Cl.
*G01N 33/53* (2006.01)
*G01N 33/564* (2006.01)
*G01N 33/569* (2006.01)
*C12Q 1/68* (2006.01)

(52) U.S. Cl. ............................ 435/7.2; 435/6; 435/7.1; 435/7.32; 435/7.37; 435/69.1; 435/69.7; 435/69.8; 435/71.1; 435/71.2; 435/320.1

(58) Field of Classification Search ............... 435/69.1, 435/6, 7.1, 7.2, 7.32, 7.37, 69.7, 69.8, 71.1, 435/71.2, 320.1
See application file for complete search history.

(56) References Cited

U.S. PATENT DOCUMENTS 5,348,867 A * 9/1994 Georgiou et al. .......... 435/69.7
5,436,228 A 7/1995 Postlethwaite et al.
5,516,637 A 5/1996 Huang et al.
5,571,698 A 11/1996 Ladner et al.
5,583,038 A 12/1996 Stover
5,587,471 A 12/1996 Cook et al.
5,846,765 A 12/1998 Matthews et al.
6,031,071 A 2/2000 Mandeville et al.
6,054,312 A 4/2000 Larocca et al.
6,057,098 A 5/2000 Buechler et al.
6,245,331 B1 6/2001 Laal et al.

FOREIGN PATENT DOCUMENTS

EP 0 765 478 B1 8/1998
EP 0 527 839 B1 12/1998
EP 0 916 726 A1 5/1999
EP 0 585 287 B1 10/1999
WO WO 96/40771 12/1996
WO WO 97/08553 3/1997
WO WO 98/37186 8/1998

(Continued)

OTHER PUBLICATIONS

Clark-Curtiss et al. Methods in Enzymology (1983) 101:347-362.*

(Continued)

*Primary Examiner*—Carla J. Myers
(74) *Attorney, Agent, or Firm*—Cooley Godward LLP

(57) ABSTRACT

A minicell display method has been developed which has significant advantages for screening peptide libraries for candidates that can bind and effectively modulate a particular biological process. The method, based on the small, anucleate minicell, has increased versatility in generating unique sequences to screen as well as increasing the size of the peptides to be screened. In vivo mutagenesis, at the level of protein synthesis, as well as DNA replication, increases diversification of the library to be screened and therefore substantially increases the number of potential peptides that can modulate a particular biological response or mechanism.

20 Claims, 1 Drawing Sheet

FOREIGN PATENT DOCUMENTS

| | | |
|---|---|---|
| WO | WO 98/54312 | 12/1998 |
| WO | WO 99/20749 | 4/1999 |

OTHER PUBLICATIONS

Puente et al. Gene (1987) 61:75-83.*

Shivakumar et al. Plasmid. 1979. 2:279-289.*

Brown et al., "A novel approach for the identification of unique tumor vasculature binding peptides using an *E. coli* peptide display library," *Ann. Surg. Oncol.*, 7(10):743-749 (2000).

Cwirla, et al., "Peptides on phage: a vast library of peptides for identifying ligands," *Proc. Natl. Acad. Sci. USA*, 87(16): 6378-6382 (1990).

De Boer, et al., "A division inhibitor and a topological specificity factor coded for by the minicell locus determine proper placement of the division septum in *E. coli," Cell,* 56(4): 641-649 (1989).

De Boer, et al., "Central role for the *Escherichia coli* minC gene product in two different cell division-inhibition systems," *Proc. Nat. Acad. Sci.,* 87(3): 1129-1133 (1990).

Devlin, et al., "Random peptide libraries: a source of specific protein binding molecules," *Science,* 249: 404-406 (1990).

"FliTrx Random Peptide Display Library for the specific identification of protein-protein interactions," Catalog No. K1125-01 by Invitroger Corporation: Carlsbad, CA.

Klemm, et al., "Fimbriae-assisted bacterial surface display of heterologous peptides," *Int. J. Med. Microbiol.* 290:215-221 (2000).

Liu, et al., "Progress toward the evolution of an organism with an expanded genetic code," *Proc. Natl. Acad. Sci. USA,* 96(9):4780-4785 (1999).

Lu, et al., "*Displaying Libraries of Conformationally Constrained Peptides on the Surface of Escherichia coli as Flagellin Fusions*," Methods in Molecular Biology 87: 265-280 (1998).

Lu et al., "Expression of thioredoxin random peptide libraries on the *Escherichia coli* cell surface as functional fusions to flagellin: a system designed for exploring protein-protein interactions," *BioTechnology,* 13(4):366-372 (1995).

Magliery, et al., "Expanding the genetic code: selection of efficient suppressors of four-base codons and identification of "shifty" four-base codons with a library approach in *Escherichia coli," J. Mol. Biol.,* 307(3): 755-769 (2001).

"Immobilized Enzymes," *Methods in Enzymology* vol. 44 (Mosbach, ed.), Academic Press: New York, (1976).

Murphy, et al., "Surface topology of the *Escherichia coli* K-12 lerric enterobactin receptor," *J. Bacteriol.,* 172(5):2736-2746 (1990).

"Production, Properties, and Utility of Bacterial Minicells," *Current Topics in Microbiology and Immunology Volume 69* (Arber, et al., eds.), New York, 1975.

Scott, et al., "Searching for peptide ligands with an epitope library," *Science,* 249(4967): 386-390 (1990).

Wang, et al., "Expanding the genetic code of *Escherichia coli," Science,* 292(5516):498-500 (2001).

Westerlund-Wlkstrom, "Peptide display on bacterial flagella: Principles and applications," *Int. J. Med. Microbiol.* 290: 223-230 (2000).

Grayson, et al., "A gene from *Renibacterium salmonarum* encoding a product which shows homolgy to bacterial zinc- metalloproteases," *Microbiology* 141(6): 1331-1341 (1995).

* cited by examiner

MINICELL DISPLAY

A Grow the Library

B Immobilize Receptor

C Incubate Library With the Receptor

D Wash off Unbound Cells

E Isolate and Identify Bound Sequence

SEQUENCE LISTING

<160> NUMBER OF SEQ ID NOS: 53

<210> SEQ ID NO 1
<211> LENGTH: 63
<212> TYPE: DNA
<213> ORGANISM: Artificial sequence
<220> FEATURE:
<223> OTHER INFORMATION: Primer 1 harboring Xba 1 site (for construction of N-terminal fragment of the 17K antigen).

-continued

<400> SEQUENCE: 1

```
tctagaatga aacttttatc taaaattatg attatagctc ttgcaacttc tatgttagcc     60

gcc                                                                   63
```

<210> SEQ ID NO 2
<211> LENGTH: 67
<212> TYPE: DNA
<213> ORGANISM: Artificial sequence
<220> FEATURE:
<223> OTHER INFORMATION: Primer 2 (for construction of the N-terminal fragment of the 17K antigen).

<400> SEQUENCE: 2

```
tcggcggaca ttgccaggcc cgccatactt atttgttcca tgtccttgtg aagaaccgcc     60

acgaccg                                                               67
```

<210> SEQ ID NO 3
<211> LENGTH: 49
<212> TYPE: DNA
<213> ORGANISM: Artificial sequence
<220> FEATURE:
<223> OTHER INFORMATION: Primer 3 (for construction of the N-terminal fragment of the 17K antigen).

<400> SEQUENCE: 3

```
ggcggtgctg gcggcgcatt acttggttct caattcggta agggcaaag                 49
```

<210> SEQ ID NO 4
<211> LENGTH: 75
<212> TYPE: DNA
<213> ORGANISM: Artificial sequence
<220> FEATURE:
<223> OTHER INFORMATION: Primer 4 harboring BamH1 site (for construction of the N-terminal fragment of the 17K antigen)

<400> SEQUENCE: 4

```
cccgtttcct gtcgaacaac ctcatccaca tccacgtaat gaacctcgtc aagaaccacc     60

tgtttagccg gatcc                                                      75
```

<210> SEQ ID NO 5
<211> LENGTH: 71
<212> TYPE: PRT
<213> ORGANISM: Artificial sequence
<220> FEATURE:
<223> OTHER INFORMATION: First 71 amino acids of the 17 K antigen of Rickettsia rickettsii

<400> SEQUENCE: 5

```
Met Lys Leu Leu Ser Lys Ile Met Ile Ile Ala Leu Ala Thr Ser Met
1               5                   10                  15

Leu Ala Ala Cys Asn Gly Pro Gly Gly Met Asn Lys Gln Gly Thr Gly
            20                  25                  30

Thr Leu Leu Gly Gly Ala Gly Gly Ala Leu Leu Gly Ser Gln Phe Gly
        35                  40                  45

Lys Gly Lys Gly Gln Leu Val Gly Val Gly Val Gly Ala Leu Leu Gly
    50                  55                  60

Ala Val Leu Gly Gly Gln Ile
65                  70
```

<210> SEQ ID NO 6
<211> LENGTH: 213

-continued

```
<212> TYPE: DNA
<213> ORGANISM: Artificial Sequence
<220> FEATURE:
<223> OTHER INFORMATION: DNA encoding the N-terminus of the 17K antigen
      of Rickettsia rickettsii.

<400> SEQUENCE: 6

atgaaacttt tatctaaaat tatgattata gctcttgcaa cttctatgtt agccgcctgt     60

aacggtccgg gcggtatgaa taaacaaggt acaggaacac ttcttggcgg tgctggcggc    120

gcattacttg gttctcaatt cggtaagggc aaaggacagc ttgttggagt aggtgtaggt    180

gcattacttg gagcagttct tggtggacaa atc                                 213


<210> SEQ ID NO 7
<211> LENGTH: 4
<212> TYPE: PRT
<213> ORGANISM: Artificial sequence
<220> FEATURE:
<223> OTHER INFORMATION: Inhibitor of macrophage recruitment.

<400> SEQUENCE: 7

Val Leu Glu Pro
1


<210> SEQ ID NO 8
<211> LENGTH: 9
<212> TYPE: PRT
<213> ORGANISM: Artificial Sequence
<220> FEATURE:
<223> OTHER INFORMATION: Inhibitor of cell/collagen interaction.

<400> SEQUENCE: 8

Asp Asp Asp Arg Lys Trp Gly Phe Cys
1               5


<210> SEQ ID NO 9
<211> LENGTH: 9
<212> TYPE: PRT
<213> ORGANISM: Artificial sequence
<220> FEATURE:
<223> OTHER INFORMATION: Inhibitor of cell/collagen interaction.

<400> SEQUENCE: 9

Asp Gln Asp Gln Arg Trp Gly Tyr Cys
1               5


<210> SEQ ID NO 10
<211> LENGTH: 9
<212> TYPE: PRT
<213> ORGANISM: Artificial sequence
<220> FEATURE:
<223> OTHER INFORMATION: Inhibitor of cell/collagen interaction

<400> SEQUENCE: 10

Asp Arg Asp Arg Ala Trp Gly Tyr Cys
1               5


<210> SEQ ID NO 11
<211> LENGTH: 7
<212> TYPE: PRT
<213> ORGANISM: Artificial sequence
<220> FEATURE:
<223> OTHER INFORMATION: Inhibitor of cell/collagen interaction.

<400> SEQUENCE: 11

Asp Arg Gln Trp Gly Leu Cys
```

-continued

```
1               5


<210> SEQ ID NO 12
<211> LENGTH: 9
<212> TYPE: PRT
<213> ORGANISM: Artificial sequence
<220> FEATURE:
<223> OTHER INFORMATION: Inhibitor of cell/collagen interaction.

<400> SEQUENCE: 12

Asp Ala Asp Gln Lys Phe Gly Phe Cys
1               5


<210> SEQ ID NO 13
<211> LENGTH: 17
<212> TYPE: PRT
<213> ORGANISM: Artificial sequence
<220> FEATURE:
<223> OTHER INFORMATION: Inhibitor of cell/collagen interaction

<400> SEQUENCE: 13

Glu Ser His Gln Lys Tyr Gly Tyr Cys Gly Gly Cys Asp Arg Asn Asn
1               5                   10                  15

Pro


<210> SEQ ID NO 14
<211> LENGTH: 10
<212> TYPE: PRT
<213> ORGANISM: Artificial sequence
<220> FEATURE:
<223> OTHER INFORMATION: Inhibitor of heparin binding.

<400> SEQUENCE: 14

Asp Ser Val Val Tyr Gly Leu Arg Ser Lys
1               5                   10


<210> SEQ ID NO 15
<211> LENGTH: 10
<212> TYPE: PRT
<213> ORGANISM: Artificial sequence
<220> FEATURE:
<223> OTHER INFORMATION: Inhibitor of heparin binding.

<400> SEQUENCE: 15

Asp Ser Val Ala Tyr Gly Leu Lys Ser Lys
1               5                   10


<210> SEQ ID NO 16
<211> LENGTH: 12
<212> TYPE: PRT
<213> ORGANISM: Artificial sequence
<220> FEATURE:
<223> OTHER INFORMATION: Inhibitor of heparin binding.

<400> SEQUENCE: 16

Asp Ser Val Ala Tyr Gly Leu Lys Ser Arg Ser Lys
1               5                   10


<210> SEQ ID NO 17
<211> LENGTH: 15
<212> TYPE: PRT
<213> ORGANISM: Artificial sequence
<220> FEATURE:
<223> OTHER INFORMATION: Cell attachment/ alpha v  beta x specific.

<400> SEQUENCE: 17
```

-continued

Thr Pro Val Val Pro Thr Val Asp Thr Tyr Asp Gly Arg Gly Asp
1 5 10 15

<210> SEQ ID NO 18
<211> LENGTH: 19
<212> TYPE: PRT
<213> ORGANISM: Artificial sequence
<220> FEATURE:
<223> OTHER INFORMATION: Cell attachment/ alpha v beta x specific.

<400> SEQUENCE: 18

Thr Pro Phe Ile Pro Thr Glu Ser Ala Asn Asp Gly Arg Gly Asp Ser
1 5 10 15

Val Ala Trp

<210> SEQ ID NO 19
<211> LENGTH: 7
<212> TYPE: PRT
<213> ORGANISM: Artificial sequence
<220> FEATURE:
<223> OTHER INFORMATION: Promotes cell entry of peptides.

<400> SEQUENCE: 19

Cys Val Val Val Leu Val Leu
1 5

<210> SEQ ID NO 20
<211> LENGTH: 5
<212> TYPE: PRT
<213> ORGANISM: Artificial sequence
<220> FEATURE:
<223> OTHER INFORMATION: Inhibits alpha 4 integrin binding.

<400> SEQUENCE: 20

Leu Asp Ser Ala Ser
1 5

<210> SEQ ID NO 21
<211> LENGTH: 9
<212> TYPE: PRT
<213> ORGANISM: Artificial sequence
<220> FEATURE:
<223> OTHER INFORMATION: Inhibits alpha 4 integrin binding.

<400> SEQUENCE: 21

Leu Asp Ser Pro Pro Ala Ala Leu Ser
1 5

<210> SEQ ID NO 22
<211> LENGTH: 8
<212> TYPE: PRT
<213> ORGANISM: Artificial sequence
<220> FEATURE:
<223> OTHER INFORMATION: Inhibits alpha 4 integrin binding.

<400> SEQUENCE: 22

Ala Ala Asp Val Glu Ser Pro Ser
1 5

<210> SEQ ID NO 23
<211> LENGTH: 14
<212> TYPE: PRT
<213> ORGANISM: Artificial sequence
<220> FEATURE:
<223> OTHER INFORMATION: Inhibits alpha 4 integrin binding.

<400> SEQUENCE: 23

-continued

Trp Thr Gly Gly Asp Asp Ser Gly Ser Pro Ser Ser Pro Ser
1 5 10

<210> SEQ ID NO 24
<211> LENGTH: 3
<212> TYPE: PRT
<213> ORGANISM: Artificial sequence
<220> FEATURE:
<223> OTHER INFORMATION: Inhibits alpha 4 integrin binding.

<400> SEQUENCE: 24

Ser Asp Val
1

<210> SEQ ID NO 25
<211> LENGTH: 14
<212> TYPE: PRT
<213> ORGANISM: Artificial sequence
<220> FEATURE:
<223> OTHER INFORMATION: Inhibits alpha 4 integrin binding.

<400> SEQUENCE: 25

Glu Pro Glu Glu Ser Asp Val Gly Gly Ala Ala Asp Tyr Pro
1 5 10

<210> SEQ ID NO 26
<211> LENGTH: 16
<212> TYPE: PRT
<213> ORGANISM: Artificial sequence
<220> FEATURE:
<223> OTHER INFORMATION: Inhibits alpha 4 integrin binding.

<400> SEQUENCE: 26

Gln Glu Ser Pro Ser Gly Thr Asp Leu Leu Val Ala Gly Ser Ser Pro
1 5 10 15

<210> SEQ ID NO 27
<211> LENGTH: 19
<212> TYPE: PRT
<213> ORGANISM: Artificial sequence
<220> FEATURE:
<223> OTHER INFORMATION: beta integrin binding.

<400> SEQUENCE: 27

Thr Pro Val Val Pro Thr Val Asp Thr Tyr Asp Gly Arg Gly Asp Ser
1 5 10 15

Leu Ala Tyr

<210> SEQ ID NO 28
<211> LENGTH: 16
<212> TYPE: PRT
<213> ORGANISM: Artificial sequence
<220> FEATURE:
<223> OTHER INFORMATION: beta 3 attachment.

<400> SEQUENCE: 28

Asp Lys Lys Glu Leu Ala Lys Phe Gln Ala Glu Arg Ser Ala Ala Ser
1 5 10 15

<210> SEQ ID NO 29
<211> LENGTH: 17
<212> TYPE: PRT
<213> ORGANISM: Artificial sequence
<220> FEATURE:
<223> OTHER INFORMATION: beta 3 attachment.

-continued

<400> SEQUENCE: 29

His Asp Arg Lys Glu Phe Ala Lys Phe Glu Glu Glu Glu Arg Ala Arg
1 5 10 15

Ala

<210> SEQ ID NO 30
<211> LENGTH: 16
<212> TYPE: PRT
<213> ORGANISM: Artificial sequence
<220> FEATURE:
<223> OTHER INFORMATION: beta 3 attachment.

<400> SEQUENCE: 30

His Asp Arg Arg Glu Phe Ala Lys Phe Gln Ser Glu Arg Ser Arg Ala
1 5 10 15

<210> SEQ ID NO 31
<211> LENGTH: 16
<212> TYPE: PRT
<213> ORGANISM: Artificial sequence
<220> FEATURE:
<223> OTHER INFORMATION: beta 3 attachment.

<400> SEQUENCE: 31

His Asp Arg Lys Glu Val Ala Lys Phe Glu Ala Glu Arg Ser Lys Ala
1 5 10 15

<210> SEQ ID NO 32
<211> LENGTH: 22
<212> TYPE: PRT
<213> ORGANISM: Artificial sequence
<220> FEATURE:
<223> OTHER INFORMATION: beta 3 attachment.

<400> SEQUENCE: 32

Gln Ser Trp Lys Lys Gln Gly Ser Pro Ser Ser Pro Gln Arg Arg Ser
1 5 10 15

Lys Gly Gly Arg Lys Pro
20

<210> SEQ ID NO 33
<211> LENGTH: 13
<212> TYPE: PRT
<213> ORGANISM: Artificial sequence
<220> FEATURE:
<223> OTHER INFORMATION: Endothelial cell attachment.

<400> SEQUENCE: 33

Ser Asp Gln Asp Asn Asn Gly Lys Gly Ser His Glu Ser
1 5 10

<210> SEQ ID NO 34
<211> LENGTH: 13
<212> TYPE: PRT
<213> ORGANISM: Artificial sequence
<220> FEATURE:
<223> OTHER INFORMATION: Endothelial cell attachment.

<400> SEQUENCE: 34

Ser Asp Gln Asp Gln Asp Gly Asp Gly His Gln Asp Ser
1 5 10

<210> SEQ ID NO 35
<211> LENGTH: 7
<212> TYPE: PRT

-continued

```
<213> ORGANISM: Artificial sequence
<220> FEATURE:
<223> OTHER INFORMATION: Fibronectin receptor binding collagenase
      induction.

<400> SEQUENCE: 35

Gly Arg Gly Asp Asn Pro Ser
1               5


<210> SEQ ID NO 36
<211> LENGTH: 17
<212> TYPE: PRT
<213> ORGANISM: Artificial sequence
<220> FEATURE:
<223> OTHER INFORMATION: Fibronectin receptor binding collagenase
      induction.

<400> SEQUENCE: 36

Leu Val Pro Ser Ser Lys Gly Arg Gly Asp Tyr Leu Ala Gln Ser Gln
1               5                   10                  15

Pro


<210> SEQ ID NO 37
<211> LENGTH: 10
<212> TYPE: PRT
<213> ORGANISM: Artificial sequence
<220> FEATURE:
<223> OTHER INFORMATION: Inhibits fibroblast attachment, inhibits
      collagenase induction.

<400> SEQUENCE: 37

Pro Asn Gly Arg Gly Glu Ser Leu Ala Tyr
1               5                   10


<210> SEQ ID NO 38
<211> LENGTH: 9
<212> TYPE: PRT
<213> ORGANISM: Artificial sequence
<220> FEATURE:
<223> OTHER INFORMATION: Inhibits melanoma cell attachment.

<400> SEQUENCE: 38

Asp Arg Tyr Leu Lys Phe Arg Pro Val
1               5


<210> SEQ ID NO 39
<211> LENGTH: 17
<212> TYPE: PRT
<213> ORGANISM: Artificial sequence
<220> FEATURE:
<223> OTHER INFORMATION: Inhibits melanoma cell attachment.

<400> SEQUENCE: 39

His Lys Phe Val His Trp Lys Lys Pro Val Leu Pro Ser Gln Asn Asn
1               5                   10                  15

Gln


<210> SEQ ID NO 40
<211> LENGTH: 8
<212> TYPE: PRT
<213> ORGANISM: Artificial sequence
<220> FEATURE:
<223> OTHER INFORMATION: Inhibits neutrophils, endothelium, fibro-
      sarcomas, melanoma attachment.

<400> SEQUENCE: 40
```

-continued

```
Lys Gly Met Asn Tyr Thr Val Arg
1               5


<210> SEQ ID NO 41
<211> LENGTH: 8
<212> TYPE: PRT
<213> ORGANISM: Artificial sequence
<220> FEATURE:
<223> OTHER INFORMATION: Inhibits endothelial cell attachment.

<400> SEQUENCE: 41

Asp Pro Gly Tyr Ile Gly Ser Arg
1               5


<210> SEQ ID NO 42
<211> LENGTH: 17
<212> TYPE: PRT
<213> ORGANISM: Artificial sequence
<220> FEATURE:
<223> OTHER INFORMATION: Inhibits endothelial cell attachment.

<400> SEQUENCE: 42

Val Leu Pro Thr Pro Thr Pro Pro Gly Tyr Leu Ser Ser Arg Ser Ser
1               5                   10                  15

Arg


<210> SEQ ID NO 43
<211> LENGTH: 15
<212> TYPE: PRT
<213> ORGANISM: Artificial sequence
<220> FEATURE:
<223> OTHER INFORMATION: Inhibits CD44 interaction with GAG.

<400> SEQUENCE: 43

Lys Asn Asn Gln Lys Ser Glu Pro Leu Ile Gly Arg Lys Lys Thr
1               5                   10                  15


<210> SEQ ID NO 44
<211> LENGTH: 20
<212> TYPE: PRT
<213> ORGANISM: Artificial sequence
<220> FEATURE:
<223> OTHER INFORMATION: Inhibits CD44 interaction with GAG.

<400> SEQUENCE: 44

Tyr Tyr Trp Arg Gln Gln Gln Lys Ser Asp Pro Val Val Ser Arg Arg
1               5                   10                  15

Arg Ser Pro Ser
            20


<210> SEQ ID NO 45
<211> LENGTH: 7
<212> TYPE: PRT
<213> ORGANISM: Artificial sequence
<220> FEATURE:
<223> OTHER INFORMATION: Anti-angiogenic.

<400> SEQUENCE: 45

Ala Thr Trp Leu Pro Pro Arg
1               5


<210> SEQ ID NO 46
<211> LENGTH: 8
<212> TYPE: PRT
<213> ORGANISM: Artificial sequence
<220> FEATURE:
```

-continued

<223> OTHER INFORMATION: Anti-angiogenic.

<400> SEQUENCE: 46

Gln Val Gly Leu Lys Pro Leu Val
1               5

<210> SEQ ID NO 47
<211> LENGTH: 14
<212> TYPE: PRT
<213> ORGANISM: Artificial sequence
<220> FEATURE:
<223> OTHER INFORMATION: Anti-angiogenic

<400> SEQUENCE: 47

Thr Pro Thr Val Arg Gly Ala Ala Gly Ser Gly Asn Gln Asn
1               5                   10

<210> SEQ ID NO 48
<211> LENGTH: 15
<212> TYPE: PRT
<213> ORGANISM: Artificial sequence
<220> FEATURE:
<223> OTHER INFORMATION: Inhibits homotypic aggregation of tumor cells.

<400> SEQUENCE: 48

His Gly Arg Phe Ile Leu Pro Trp Trp Tyr Ala Phe Ser Pro Ser
1               5                   10                  15

<210> SEQ ID NO 49
<211> LENGTH: 9
<212> TYPE: PRT
<213> ORGANISM: Artificial sequence
<220> FEATURE:
<223> OTHER INFORMATION: Anti-adhesion (cell-cell).

<400> SEQUENCE: 49

Lys Lys Ala Lys Lys Ser Arg Arg Ser
1               5

<210> SEQ ID NO 50
<211> LENGTH: 9
<212> TYPE: PRT
<213> ORGANISM: Artificial sequence
<220> FEATURE:
<223> OTHER INFORMATION: Anti-adhesion (cell-cell).

<400> SEQUENCE: 50

Lys Lys Gly Lys Lys Ser Lys Arg Ser
1               5

<210> SEQ ID NO 51
<211> LENGTH: 20
<212> TYPE: PRT
<213> ORGANISM: Artificial sequence
<220> FEATURE:
<223> OTHER INFORMATION: Anti-adhesion (cell-cell)

<400> SEQUENCE: 51

Arg Arg Ser Arg Ser Ser Thr Gly Lys Lys Gln Lys Ser Ser Gln Ser
1               5                   10                  15

Arg Lys Thr Ala
            20

<210> SEQ ID NO 52
<211> LENGTH: 43
<212> TYPE: PRT

-continued

```
<213> ORGANISM: Artificial sequence
<220> FEATURE:
<223> OTHER INFORMATION: Apoptotic to tumor cells.

<400> SEQUENCE: 52

Asp Gly Gly Arg Gly Asp Ser Leu Gly Trp Tyr Arg Arg Gly Arg Gly
1               5                   10                  15

Gly Ala Arg Arg Ser Lys Ala Lys Lys Ala Ala Ala Lys Asn Asn Gln
            20                  25                  30

Lys Ser Glu Pro Leu Ile Gly Arg Lys Lys Thr
        35                  40


<210> SEQ ID NO 53
<211> LENGTH: 4
<212> TYPE: PRT
<213> ORGANISM: Artificial sequence
<220> FEATURE:
<223> OTHER INFORMATION: Apoptotic to tumor cells.

<400> SEQUENCE: 53

Lys Arg Ser Arg
1
```

METHODS TO SCREEN PEPTIDE LIBRARIES USING MINICELL DISPLAY

CROSS REFERENCE TO RELATED APPLICATIONS

Priority is claimed to U.S. Provisional Application Ser. No. 60/274,039 filed on Mar. 7, 2001, and U.S. Provisional Application Ser. No. 60/306,946 filed on Jul. 20, 2001.

FIELD OF THE INVENTION

The present invention is generally in the field of high throughput peptide screening, and in particular relates to a minicell display technology for generation and screening of random peptides.

BACKGROUND OF THE INVENTION

The interaction between cognate proteins in receptor-ligand complexes, enzyme substrate reactions and antibody-antigen binding reactions has furthered the understanding of the molecular interactions required to effect a response in a wide range of processes. The search for new peptide molecules which can bind to selected targets and effectively modulate a particular biological process is at the forefront of agricultural, biological, and medicinal research.

There are several examples of methods that use peptides or nucleotides to develop libraries of potential receptor, enzyme, or antibody interacting peptides. Over the course of the last two decades these libraries have been incorporated into systems that allow the expression of random peptides on the surface of different phage or bacteria. Many publications have reported the use of phage display technology to produce and screen libraries of polypeptides for binding to a selected target. See, e.g, Cwirla et al., Proc. Natl. Acad. Sci. USA 87, 6378–6382 (1990); Devlin et al., Science 249, 404–406 (1990), Scott & Smith, Science 249, 386–388 (1990); U.S. Pat. No. 5,571,698 to Ladner et al. A basic concept of phage display methods is the establishment of a physical association between DNA encoding a polypeptide to be screened and the target polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

In addition to providing a method for selecting peptides that interact with target molecules, phage display has been used to direct filamentous phage to target cells using peptides, genetically fused to phage coat proteins, that bind integrin proteins on the surface of mammalian cells. This method of phage display has had a profound influence on gene therapy applications and their attempts to target cells in a specific manner.

Another approach to obtaining surface expressed foreign proteins has been the use of bacterial native membrane proteins as carriers for foreign protein. In general, many attempts to develop methods of anchoring proteins on a bacterial surface have focused on fusion of the desired recombinant polypeptide to a native protein that is normally exposed on the cell's exterior with the hope that the resulting hybrid will also be localized on the surface. However, in most cases, the foreign protein interferes with localization, and thus, the fusion protein is unable to reach the cell surface. These fusions either end up at incorrect cellular locations or become anchored in the membrane with a secreted protein domain facing the periplasm. See Murphy, et al., J. Bacteriol., 172:2736 (1990).

Recent advances in bacterial display methods have circumvented this problem by using fusion proteins comprising pilin protein (TraA) or a portion thereof and a heterologous polypeptide displaying the library peptide on the outer surface of the bacterial host cell capable of forming pilus. See U.S. Pat. No. 5,516,637 to Huang et al. The pilus is anchored to the cell surface of the bacteria and is naturally solvent exposed.

Alternatively, the FLITRX™ (Invitrogen Corp.) random peptide library uses the bacterial flagellar protein, FliC, and thioredoxin, TrxA, to display a random peptide library of dodecamers on the surface of *E.coli* in a conformationally constrained manner. See Lu et al., BioTechnology, 13:366 (1995). These systems have been applied to antibody epitope mapping, the development and construction of live bacterial vaccine delivery systems, and the generation of whole-cell bio-adsorbants for environmental clean-up purposes and diagnostics. Peptide sequences that bind to tumor specific targets on tumor derived epithelial cells have also been identified using the FLITRX™ system. See Brown et al., Annals of Surgical Oncology, 7(10):743 (2000).

Although the phage and bacterial display systems have provided unique routes to elucidating new peptides which can bind target molecules with new or enhanced binding properties, there are several important limitations that need to be considered. Minimal changes in the structural conformation of the phage coat protein to which the peptide is genetically fused are tolerable. Problems arise when larger peptide inserts (more than 100 amino acids) disrupt the function of the coat protein and therefore phage assembly. Heterologous peptides have been displayed on bacteria using both fimbriae as well as flagellar filaments. Insert size constraints affect the applicability of these systems as well. To date, the largest peptides to be displayed in fimbriae range from 50 to 60 amino acids, while the functional expression of adhesive peptides fused to the FliC flagellin of *Escherichia coli* appears to be restricted to 302 amino acids. See Westerlund-Wikstrom 2000.

Amino acid analogs have been used to replace chemically reactive residues and improve the stability of the synthetic peptide as well as to modulate the affinity of drug peptide compounds for their targets. A limitation of the phage and bacterial display systems resides in the inability of these systems to incorporate amino acid analogs into peptide libraries in vivo. In vivo, amino acid analogs disrupt the cellular machinery used to incorporate natural amino acids into essential proteins as well as the growing peptide chain of interest. Phage and bacterial display both rely on the protein synthesis machinery of the bacterial cell to synthesize proteins essential for viability, synthesize the peptide library, and amplify or propagate the phage or bacterial pool harboring the peptide of interest. Technically cumbersome protocols can be time consuming when attempting the in vitro translation methods frequently used to incorporate amino acid analogs into a peptide sequence.

The method of propagating the phage or bacterial pool requires expression of the peptide of interest. Peptides that are toxic to the bacterial cell and therefore lethal cannot be screened for in phage or bacterial display systems. This eliminates a potentially large segment of peptides that otherwise would be of interest.

Phage and bacterial display also rely upon cumbersome and time consuming techniques in order to keep conditions optimal for cell growth and cell viability. Bacterial cells are relatively large and care must be taken while screening for target interacting peptides. Affinity chromatography is a common method used to separate non-binding peptides from binding peptides and care must be taken to prevent plugging and the non-specific retention of bacteria in the column. Candidate peptide displaying phage are generally amplified or propagated and therefore require the use of the cellular transcriptional, translational, and replication machinery of bacteria to synthesize the packaging proteins of the phage as well as the peptide of interest. Infecting bacterial cells, harvesting the phage, and re-infecting several rounds is very time consuming. The bacterial cell display system also requires optimal growth conditions to ensure safe passage of the plasmid encoded peptide from generation to generation and for subsequent re-screening.

Oligonucleotide-mediated mutagenesis has been utilized to further characterize selected peptides. Generally, oligonucleotide-mediated mutagenesis is used to introduce very specific mutations into the gene of interest. Although the selection of specific mutations to be introduced into the gene is usually based on published reports describing the effects of the mutations on the activity or function of other homologous proteins, it is still difficult to predict the affect of the mutation or substitution.

It is often advantageous to increase the spontaneous mutation frequency of the peptide library in vivo. Increasing the diversity of a population of peptides displayed on a bacterial surface has proven to be a very useful tool for identifying those with a particular effect. Spontaneous mutations maintain evolutionary pressure on the peptide library and maximize the screening of unique sequences.

A display system that is amenable to the uncomplicated nature of cloning and amplification of DNA sequences using the genetics of bacteria, for example *E. coli,* to increase the variability and size of the peptides within the library is desirable. There is a need to generate novel peptide libraries in a system that will allow the in vivo incorporation of amino acids analogs into the oligonucleotide sequence such that its genetic and biochemical characteristics are altered. There is a need for generating peptides that may otherwise be eliminated by virtue of their toxicity in phage or bacterial display systems. There is also a need to manipulate the oligonucleotide in vivo and yet alleviate the requirement to ensure optimal growth conditions for cell viability.

It is therefore an object of this invention to provide an effective and rapid method for the systematic preparation of novel peptide substrates having altered functional and binding activity and to address the shortcomings inherent in the phage and bacterial display methods currently practiced in the art.

BRIEF SUMMARY OF THE INVENTION

Methods for selecting oligonucleotides and peptides of interest, and generating and screening large mini-cell display libraries for peptides with desired functional and binding characteristics have been developed. These methods include selecting new and unique target interacting peptides from minicell display libraries of random oligonucleotides that are expressed as gene fusions to a protein such as the 17K antigen of *Rickettsia rickettsii.*

The plasmid or expression vector encoded oligonucleotide fusion or gene fusion product is preferably localized to the minicell outer membrane forming what is referred to as a "display minicell". Briefly, the method consists of first constructing a library wherein the library consists of a replicable expression vector includes an inducible transcriptional regulatory element operably linked to a gene fusion, where the gene fusion includes:

(i) a first gene encoding at least a portion of a bacterial outer membrane protein; and (ii) a second gene or oligonucleotide encoding a potential "substrate" peptide interacting with a target molecule.

The 3' end of the first gene is linked to the 5' end of the second gene or oligonucleotide, thereby forming a chimeric gene. The chimeric gene encodes a chimeric protein. The linkage between the first and second gene may be direct, or indirect via a linker molecule or oligonucleotide. The second gene or oligonucleotide is obtained from a library of random oligonucleotides constructed by degenerate polymerase chain reaction (PCR), a method well known within the art, or other amplification method.

In certain embodiments, it is desirable that the first gene encodes an outer membrane protein, or portion thereof, amenable to fusing large oligonucleotides encoding proteins greater than 302 amino acids in length. The 17K antigen of *Rickettsia rickettsii* is preferred. In one embodiment the expression of the fusion protein is regulated by an inducible DNA regulatory element, for example, a lac promoter, tac promoter (a hybrid trp-lac promoter that is regulated by the lac repressor), trp promoter, or lacUV5 promoter. Other suitable microbial promoters may be used as well. By using an inducible promoter, the oligonucleotide fusion will remain quiescent until the addition of the inducer. This allows control of the timing of production of the gene product.

The method further includes mutating the expression vector at one or more selected positions within the second gene, thereby forming a family of related substrate peptides encoded by the second gene. Next, suitable host minicell strains are transformed with the expression vector DNA preparation. The method also provides for the induction of replication of the acquired plasmid DNA and the controlled expression of the corresponding peptide within the minicell.

Optionally, the method consists of transforming suitable host minicell strains exhibiting a mutator phenotype and subsequent induction of the minicells to replicate acquired plasmid DNA. The method further includes generating a bacterial minicell strain exhibiting mutator phenotype. Mutations in genes responsible for DNA repair typically have a mutator phenotype. For example, mutations in the genes responsible for the methyl-directed mismatch repair of DNA, designated mutS, mutL, and mutH, increase the spontaneous mutation frequency about 1000-fold. Incorporating one, two, or all three of these mutations into the parent bacterial cell results in the in vivo diversification of the peptide display library within the anucleate minicell population.

The minicells are subsequently induced to express the library of peptides on their outer surface. The pre-selected target molecules are then contacted with the display minicells and the peptide library is screened for binding activity by methods well established within the art.

The pre-selected target molecule can be a protein, peptide, carbohydrate, sugar, nucleic acid, metal, or non-protein organic molecule, such as a drug, vitamin or co-factor, neuromediator, cell receptor or cell receptor complex, steroid, peptide mimicking a natural acceptor binding site to a pre-selected molecule or an analog thereof, or an individual protein of a receptor complex.

In another embodiment, functional screening assays are incorporated to establish biochemical activity relating to, for example, inhibitory, stimulatory, or responsive processes associated with the peptide of interest.

Those minicells that bind to the target molecule are separated from those that do not. Optionally, the peptides displayed on the minicells may be labeled with molecules or compounds such as radioactive isotopes, rhodamine, or FITC before, during, or after expression of the display library. This serves to facilitate subsequent identification of the bound peptide of interest. For example, antibodies available to the target molecule may be used to immunoprecipitate the interacting complex. If the interacting peptide is radiolabeled, the complex can be easily distinguished and visualized by autoradiography, a method well established within the art. Optionally, the minicells may be supplemented exogenously with amino acid analogs to be incorporated into the peptide being synthesized in vivo.

The bound minicell library members that have been separated from the unbound members now represent an enriched library. The expression vectors that contain the oligonucleotides of this enriched library can be isolated, mutagenized and displayed again to screen for altered specificity of the fusion protein towards the target. Alternatively, the enriched library may be tested again, under more stringent conditions, for binding ability, those that bind are separated from those that do not and the library is further enriched.

This method may be repeated one or more times with either the minicells that bound to the target molecule or those that did not.

The bound minicells can be easily eluted from the target molecule and the peptide encoding expression vectors isolated to extract information. The DNA sequence of the peptide, DNA base composition, the molecular weight, and/or whether any secondary structures exist within the sequence can then be determined.

Optionally, the method comprises liberating the peptide of interest from the display protein, to which it is genetically fused, for subsequent amino acid analysis. Amino acid analysis of the peptide library is carried through by methods well known within the art using automated analyzers. One can also determine the amino acid composition, the amino acid sequence, the isoelectric point, and molecular weight of the peptide.

These peptides can then be further screened for desired activities. Further rational manipulation can also be performed to delete, add, or substitute specific amino acids or to label the peptide or to immobilize the peptide for use in diagnostic screening assays.

DETAILED DESCRIPTION OF THE INVENTION

Figure 1:
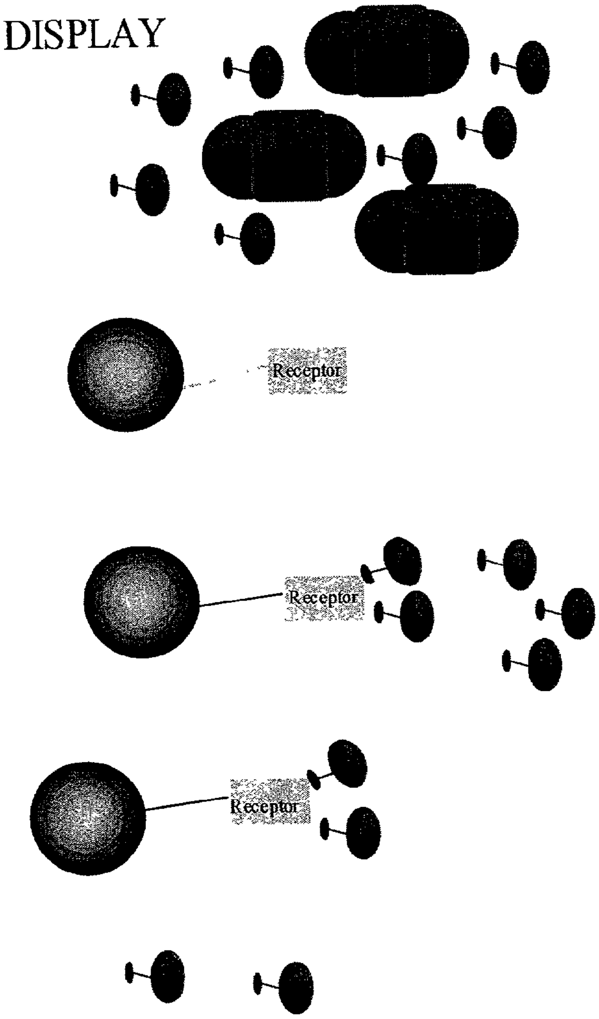
FIG. 1 is a flow chart of the strategy for displaying random library peptides on the surface of minicells.

I. Minicell construction and composition.

Minicells offer an alternative method for packaging library DNA and displaying peptides. As used herein, the terms "peptide" and "protein" are used interchangeably unless otherwise noted. Minicells are small, anucleate cells resulting from aberrant cell divisions at the polar ends of bacteria. However, the minicells are large enough to harbor several plasmids and have been extensively used to analyze cloned protein expression since they lack bacterial chromosomal DNA, but contain all of the necessary machinery for coupled transcription and translation, and protein modification. Many mutant bacterial strains, representing gram positive and gram negative strains, are capable of producing minicells throughout their respective cell cycles. Examples include *E. coli, S. typhimurium, S. anatum, S. enteritidis, S. pullorum, S. senftenberg, S. worthington, B. subtilis, V. cholera, E. amylovora,* and *H. influenzae.*

A) Min mutations.

Bacterial cells have been provided with an elegant system to control cell division. The min genes provide bacteria with the ability to control where, anatomically, cell division will take place. When bacteria normally divide, min proteins (MinC, MinD, and MinE) accumulate at the two polar ends of each cell. The min proteins prevent the cell division apparatus from accumulating at the ends of each cell and can be thought of as polar cell division inhibitors. MinE provides the topological specificity required for correct localization of the MinC and MinD proteins to the cell poles. See de Boer et al., Proc. Nat. Acad. Sci., (87) 1129–1133 (1990) or de Boer et al., Cell, (56) 641–649 (1989). With the polar ends of each cell blocked from division apparatus assembly, the proteins required for division accumulate in the middle of the cell (midcell). Cells lacking any of the minC or minD genes, or overexpressing the MinE protein, aberrantly divide at the polar ends with increased frequency, forming chromosomal DNA deficient minicells. The formed minicells, while unable to divide, are able to incorporate nucleotides into replicating plasmid DNA and synthesize protein encoded by the sequences of the plasmid. Any bacterial strain capable of forming minicells can be used as a bacterial host for the expression of the display peptide.

The principle components of the bacterial minicell strain include mutation(s) in gene(s) that confer the minicell phenotype. The mutations are preferably in a genetically clean genomic background (only those mutations conferring desired phenotype(s) are present in an otherwise wild-type background).

B) Mutator mutations.

In another embodiment, an in vivo method for further randomizing libraries of diverse oligonucleotides and the peptides encoded by them is used. A mutation in the mutS gene that renders the encoded protein non-functional also renders the cells harboring the mutation incapable of correcting mistakes made during DNA synthesis/replication. A mutS strain will confer a mutator phenotype.

The peptide libraries can be further diversified in vivo utilizing mutations in one of the min genes, for example minC, and transducing the mutant gene into a mutS cell line. The newly created cell line (MsMc) harbors mutations in both mutS and minC genes. Using techniques such as calcium chloride transformation or electroporation, the oligonucleotide harboring plasmid can be introduced into the new cell line. The transformed cell line may be induced to replicate plasmid DNA, by exogenously adding nucleotides, and in doing so the replication machinery of the minicell will incorporate or substitute a mis-base paired nucleotide at a rate of approximately one per one thousand bases copied or replicated. Therefore, $5\times10^8$ bacteria will generate $10^5$ new sequences every generation. The plasmids can then be transferred to a non-mutator minicell strain for further display.

C) Amino Acid Analogue Incorporation

Providing display minicells with amino acid analogues to be incorporated into the peptide of interest can be used to further diversify the library. In order for amino acid analogues to be incorporated into the peptide, the tRNA molecules involved in synthesizing the peptide from mRNA must be modified. tRNA molecules serve to chemically link themselves to a particular amino acid and then present the amino acid, corresponding to the correct sequence in the mRNA, for incorporation into the peptide chain. Twenty aminoacyl-tRNA synthetase enzymes, each corresponding to one of the twenty naturally occurring L-amino acids, add amino acids to accepting tRNA molecules. Mutations may be incorporated into any one, several, or all, of the genes encoding the aminoacyl-tRNA synthetases of the MsMc strain that will allow them to recognize and transfer analogues of amino acids to corresponding tRNA molecules. The resultant tRNA molecules then have the ability to incorporate an amino acid analogue into the growing peptide chain. Alternatively, the tRNAs may be genetically constructed to be recognized only by the synthetases that will aminoacylate with the amino acid analogue and be directed to recognize nonsense codons (suppressor tRNAs) or four base codons. See Magliery et al., J. Mol. Biol., March 2001, 307(3): 755–769. Such a combination will provide for specific in vivo incorporation of an amino acid analogue (Wang et al., Science, April 2001, 292:498–500; Liu and Schultz, Proc. Natl. Acad. Sci. USA, April 1999, 96:4780–4785). Amino acid analogues such as any hydroxyamino acid or derivative thereof, ornithine, azitryptophane, or D-amino acids can be supplied exogenously to the cells to be incorporated into the peptide chain. Alternatively, any minicell strain may harbor mutations in genes encoding the tRNA molecules.

II. Plasmid Construction.

Generally, the plasmid used is able to serve as a cloning vector that is suitable for replicating in the desired host strain. The origin of replication and control sequences are compatible with the host minicell to be used for display. For example, the plasmids pUC19 or pBR322, or derivatives thereof, may be used if *E. coli* is the strain (parent) from which the minicells are derived. The plasmids preferably include a selectable marker gene or genes that is able to be selected in the parent host. A selectable marker gene includes any gene that confers a phenotype on the parent cells to be selectively grown. Examples of selectable marker genes include, but are not limited to, the tetratcycline gene, the kanamycin gene, the ampicillin gene, and the gentamycin gene. It is preferred that the plasmid contain an inducible regulatory element for the controlled expression of sequences of interest. The plasmid should also be amenable to cloning DNA oligonucleotides, for example, ranging in length from 9 base pairs to 3000 base pairs, and be able to serve as a template for expression of oligonucleotide fusion proteins. The plasmid should also exist in multiple copies within the host cell typically ranging from 2 to 100 copies per cell.

III. Peptide Fusion Construction

A peptide capable of binding a target molecule is obtained from a random minicell library wherein the minicells express fusion proteins including at least one random peptide sequence joined to a protein exposed on the outer surface of the minicell. The fusion may be direct, or indirect via linker sequences. Indirect linkage can be represented by the direct chemical coupling between the outer membrane protein and the substrate peptide. For example, one of ordinary skill in the art will realize the plethora of nucleic acid linkers commercially available and, alternatively, available by de novo construction (it is not necessary that such a linker represent a sequence of amino acids that is normally found on the surface of a cell).

The fusion (chimeric) protein to be displayed on the surface of the minicell is generally cloned into the plasmid expression vector from which the chimeric gene encoding the chimeric protein will be expressed.

A) First gene.

The peptide to be used to direct the second gene product to the minicell surface is usually selected because it encodes a signal amino acid sequence capable of mediating correct localization of the fusion, or chimeric, protein to the outer surface of the minicell. Signal sequences include, for example, ompA signal sequence, ompT signal sequence, ompF signal sequence, ompC signal sequence, beta lactamase, the traA signal sequence, the phoA signal sequence, and the 17K antigen signal sequence of *Rickettsia rickettsii*. Furthermore, peptides harboring signal sequences that are not normally associated with the outer membrane may be modified with lipid modification consensus sequences to ensure attachment to the outer membrane.

A preferred peptide consists of the first 71 amino acids (213 nucleotides) of the 17K antigen open reading frame (ORF) of *R. rickettsii,* contains the signal sequence as well as a lipid modification site. The 213 base-paired oligonucleotide (SEQ ID NO:6) may be assembled by annealing different regions of primers corresponding to overlapping regions of the first 213 nucleotides, forming a concatamer of DNA. Single stranded portions of the concatamer are subsequently converted to double strands by purified enzymes known in the art. The resulting double stranded DNA can then be cloned into the appropriate plasmid expression vector to generate a genetic fusion to an inducible regulatory promoter element. Such a process may be used to clone any nucleic acid sequence encoding a peptide that localizes to the outer membrane of the minicell. The membrane protein encoding sequence, for example, the 213 nucleotide fragment encoding the first 71 amino acids of the 17K antigen ORF, is preferably positioned downstream of the promoter and upstream of the oligonucleotide (second gene) encoding the peptide of interest. Any termination sequence that is recognized by the expression machinery of the minicell may be used to terminate transcription. It is well known in the art that bacterial DNA sequences, and plasmid DNA sequences, rely upon one of two basic types of transcription termination, factor independent and factor dependent (based upon whether the RNA polymerase requires more than just the sequence to terminate). Such termination sites are applicable to the disclosed constructs.

B) Peptide to be targeted (second gene).

The oligonucleotide library encoding the randomized peptide to be targeted can be synthesized in vitro using PCR or other amplification methods that are well established within the art. In the preferred embodiment, the library includes at least about $10^{10}$ oligonucleotides which encode the peptides. Generally, the oligonucleotide libraries include a unique or variable sequence region which confers diversity to the library. Diversification of the library is typically achieved by altering the coding sequence which specifies the sequence of the peptide such that a number of possible amino acids can be incorporated at certain positions. At the core of creating the library lies the construction of degenerate primers. Degenerate primers can be constructed using available automated polynucleotide synthesizers, such as one of the Nucleic Acid Synthesis Instrument Systems (Applied Biosystems).

Primer sequence may be made up of a specific series of nucleotides or their equivalent IUB codes (for example, R {A,G}, W {A,T}, K {G,T}, M {A,C}, S {G,C}, V {A,G,C}, D {A,G,T}, H {A,C,T}, B {G,C,T} and N {A,G,C,T}). Many systems have been programmed to recognize IUB ambiguity codes such that an input sequence of DDDD would correspond to a four base primer sequence with each position having an equal probability of an A, G, or T incorporated. Once constructed, the randomized primers will contain regions of complementarity, within their sequence, to other primers. The complementary primers are annealed forming concatamers of nucleotide sequence whose single stranded gaps are filled in with nucleotides and polymerase to form randomized double stranded oligonucleotides. The double stranded oligonucleotides can then be cloned into the expression plasmid downstream of the inducible promoter and preferred 17K antigen to form the chimeric gene fusion.

Alternatively, oligonucleotides may be mutagenized in vitro using well known methods in the art. In vitro mutagenesis of oligonucleotides, oligonucleotides encoded within a plasmid, or gene fusions harboring the oligonucleotide in a vector or plasmid, may be site directed or random. The mutagenized plasmid can then be used to transform the minicells or minicell strain for subsequent induction of expression and screening for binding activity of the encoded peptide.

In another preferred embodiment, the bacterial minicell strain is transformed with the newly constructed plasmid. Transformation methods include, for example, phage transfection (e.g. P1, lambda, or M13), electroporation, and transformation. It is preferred that the parent minicell strain be transformed, selected via a selectable marker on the plasmid, and minicells isolated from the parent strain harboring the plasmid. Alternatively, the isolated minicells from a parent strain may be directly transformed.

IV. Minicell Isolation and Display Induction

A) Minicell Purification

In a preferred embodiment, cells harboring one or more min mutations that have undergone the desired asymmetric cell division (polar cell division) are separated from those that have not. Minicells are separated from whole bacterial cells based on their difference in size and density. Density gradient centrifugation is used to separate and isolate minicells from the population of "whole" cells present in the culture. Isolated minicells remain stable and active for 48 hours at room temperature or up to 6 weeks at −70° C. Room temperature stability eliminates the need for time consuming protocols that are required to keep whole cells and phage growing in optimal conditions throughout display methods known in the prior art. Minicells are physiologically not capable of cell division.

B) Replication of Plasmid DNA.

In a preferred embodiment, the transformed minicells are induced to replicate the plasmid DNA by exogenously adding nucleotides required for incorporation into the growing DNA strand. Replication of the plasmid DNA increases the plasmid copy number within the cell. If the transformed cells harbor a mutator phenotype the diversity of the peptides to be displayed on the outer surface will increase. The mutator phenotype exhibits its effects at the nucleotide level of DNA synthesis compared to another diversification technique, the incorporation of amino acid analogues at the level of peptide synthesis.

C) Induction of Chimeric Protein Expression.

The expression of the peptide to be displayed is under the control of an inducible promoter. Many inducible promoters are available in the art for controlling gene expression and can be used herein. Inducible promoters are ideal for the expression of peptides that would otherwise be toxic to normally dividing bacterial cells. The toxic peptides that would normally kill a dividing cell cannot exert their lethal effects within the minicell. Minicells are not growing, or dividing, and lack chromosomal DNA. Minicells are isolated and subsequently induced for expression of the chimeric peptide. The induction is usually carried out by exogenously supplying the minicells with amino acids and an inducer that will activate protein expression. For example, addition of the inducer isopropylthiogalactoside (IPTG) will relieve repression of genes under the control of lac, tac, or lacUV5 promoters. These promoters are negatively regulated by the lacI repressor protein when the addition of IPTG is omitted. The exogenously added amino acids provide the subunits required for growth of the peptide chain. Optionally, amino acid analogues may be added simultaneously or in place of the L-amino acids to further diversify the peptide library to be displayed.

V. Interactions Between Peptides to be Screened and Target or Binding Molecules ("binding partners").

The displayed peptide and interacting molecule or target are screened for an interaction. The interaction requires binding between the peptide encoded by the second gene and the target molecule. The peptide may be a substrate, cofactor, ligand, or effector. The target molecule may be a peptide or protein, nucleic acid molecule, carbohydrate or sugar, vitamin cofactor, metal, or synthetic drug. The target molecule may be a substrate for an enzyme, a cofactor that forms part of a functional complex, an enzyme which acts on the peptide encoded by the second gene, or a ligand or receptor interacting with the peptide encoded by the second gene. Examples of such target molecules include peptide interacting pairs which include antigen-antibody, biotin-avidin, hormone-hormone receptor, receptor-ligand, enzyme-substrate, IgG-protein A. The target molecule that interacts with the displayed peptide may alternatively be part of a library of random peptides. Preferably, the strength of the binding reaction is sufficient to allow the interacting pair to be isolated based on the physical reaction between the target and the random peptide. A pre-selected "target" molecule can be a drug, vitamin neuromediator, cell receptor or cell receptor complex, steroid hormone, metal, carbohydrate, inorganic or organic compound, peptide mimicking a natural acceptor binding site to a pre-selected molecule or an analog thereof, or an individual protein of a receptor complex.

VI. Separating Bound Minicells from Unbound Minicells.

In methods analogous to affinity chromatography, the pre-selected target molecule, or library of random peptides, (binding partner(s)) may be immobilized by attaching it to a suitable solid support matrix such as agarose beads, acrylamide beads, cellulose, neutral and ionic carriers, or various acrylic polymers. Methods used to attach the pre-selected molecule or library to a particular matrix are well established within the art and described, for example, in Methods in Enzymology, 44 (1976). After attachment of the molecule or peptides to the matrix, the isolated display minicells are incubated with the matrix, allowing contact to be made between the minicell and the binding partner. Unbound cells are washed away and the minicell bound to the pre-selected target may be eluted by a variety of methods including adjusting pH conditions, ionic conditions or by competing with excess free antigen. Elution conditions that may otherwise be detrimental to bacterial growth and vitality may be incorporated when eluting display minicells. Growth and vitality are not at issue with minicells. The relatively large size of bacterial cells may also preclude one from using affinity chromatography because of plugging of columns used in the technique. The smaller size of minicells is amenable to affinity chromatography.

VII. Peptide Analysis.

The displayed peptide library may be analyzed to determine the diversity and/or composition of the amino acids incorporated. Minicells may be subjected to enzymes or acids known to specifically cleave between certain peptide residues to release the peptide of interest from the display chaperone protein (for example, formic acid cleaves peptide bonds between proline and glycine residues). The peptides are then hydrolyzed and analyzed for amino acid content using automated amino acid analyzers.

The peptides may also be analyzed for precise amino acid sequence. For example, the classic method of Edman degradation, in which the N-terminus of the peptide becomes modified, cleaved, and analyzed, thus shortening the peptide by one amino acid, is one way of extracting information at the amino acid level. Mass spectrometry is a more sophisticated technique and amenable to analyzing peptides that have incorporated amino acid analogues. Mass spectrometry utilizes helium gas to randomly cleave the peptide and subsequent analysis of the mass of the fragments generated are compared to elucidate the sequence. The peptide sequence can then be used to determine and/or design oligonucleotides encoding the peptides.

VIII. Oligonucleotide (second gene) Analysis.

Because minicells are amenable to the uncomplicated nature of bacterial genetics, it is relatively easy to isolate the plasmid expression vector from the minicell by methods known to those skilled in the art and, if desired, to further propagate the plasmid in a suitable host. Alternatively, the second gene sequence contained within the isolated expression vector may be directly amplified by PCR and sequenced, using primers to known sequence within the 17K antigen (first gene) and/or the parent expression vector.

Once isolated, the plasmid expression vector may be mutagenized in vitro to study the effects of specific mutations in the genes encoding the peptide of interest. Such effects can be assayed genetically, or biochemically, as discussed below. Site directed and random mutagenesis of plasmids and vectors are well established in the art.

In another embodiment, the method uses a vector suitable for fusing oligonucleotide libraries with the display "chaperone" DNA. The preferred chaperone DNA encodes the 17K antigen of *Richettsia rickettsii.*

IX. Screening Peptides for Activity.

The peptides are preferably isolated or identified based on binding. The peptides may also, or alternatively, be screened for bioactivity. A bioactivity can be any biological effect or function that a peptide or protein may have. For example, bioactivities include specific binding to biomolecules (for example, receptor ligands), hormonal activity, cytokine activity, and inhibition of biological activity or interactions of other biomolecules (for example, agonists and antagonists of receptor binding), enzymatic activity, anti-cancer activity (anti-proliferation, cytotoxicity, anti-metastasis), immunomodulation (immunosuppressive activity, immunostimulatory activity), anti-infective activity, antibiotic activity, antiviral activity, anti-parasitic, anti-fungal activity, and trophic activity. Bioactivity can be measured and detected using appropriate techniques and assays known in the art. Antibody reactivity and T cell activation can be considered bioactivities. Bioactivity can also be assessed in vivo where appropriate. This can be the most accurate assessment of the presence of a useful level of the bioactivity of interest. Enzymatic activity can be measured and detected using appropriate techniques and assays known in the art.

As demonstrated by Example 9, several (second gene) peptides that bind to receptors that are found on the cell surface and are required for tumor metastasis have been identified using this system. These potential metastasis blocking peptides have been further evaluated for effecting a particular response on the receptor that can be assayed biochemically. Peptides have been shown to influence the autophosphorylation of receptors in vitro, by assaying the amount of radiolabeled phosphate retained by the receptor before and after interaction with the peptide. This can be shown using standard techniques within the field of molecular biology. By influencing the phosphorylation of cell surface receptors the isolated peptides can directly influence the activity of the cellular processes these receptors control. Methods are well established in the art that allow post translational, or peptide modification, of the isolated peptides in vitro. Such modifications include, but are not limited to, acylation, methylation, phosphorylation, sulfation, prenylation, glycosylation, carboxylation, ubiquitination, amidation, oxidation, hydroxylation, adding a seleno-group to amino acid side chains (for example, selenocysteine), and fluorescent labeling.

Further in vitro analyses are used to study the effects of the peptides on cell viability. Peptides that either interrupt, stimulate, or decrease vital cellular processes may be used to infect cells, such as tumor cells, in culture. Once infected, cell growth and viability is analyzed by methods known in the art.

Many cells may undergo programmed cell death which is a genetically mediated form of self destruction. This phenomenon is commonly referred to in the art as apoptosis. Frequently, apoptotic cells may be recognized by changes in their biochemical, morphological and molecular features. Morphological changes include, but are not limited to, cell shape change, cell shrinkage, cell detachment, apoptotic bodies, nuclear fragmentation, nuclear envelope changes and loss of cell surface structures. Biochemical changes may include proteolysis, protein cross linking, DNA denaturation, cell dehydration, intranucleosomal cleavage and a rise in free calcium ions. Such characteristics are easily identifiable by methods well established in the art. Peptides isolated by the disclosed mini-cell display method are tested for their effects on such physiological and biochemical processes.

When cells are no longer viable, i.e. they are dead, their membranes become permeabilized and this permeabilization will manifest itself as a change in the scattering of light. This scattering of light can be attributed to the change in the refractive index of the cell's cytoplasm. The use of DNA staining dyes that are able to pass through a permeabilized membrane, will aid in the identification of dead, live, and apoptotic cells. Flow cytometry and/or fluorescent activated cell sorting (FACS analysis) may be incorporated into protocols utilizing fluorescent dyes to separate the cells of interest. Flow cytometry can sort, or physically separate, particles of interest from a sample. Therefore, FACS analysis (which is a type of flow cytometry), may be defined as the physical separation of a cell or particle of interest from a heterogeneous population.

One may distinguish between dead, live, and apoptotic cells because each differ, for example, in their permeability to DNA dyes. Two widely used DNA dyes, Hoechst 33342 and propidium iodide (PI), are able to infiltrate dead cells. Live cells do not retain either dye, while apoptotic cells are able to retain Hoechst but not PI. Fluorescent microscopic observation will allow one to visually separate dead cells from live cells from cells undergoing apoptosis. Fluorescence emission from these different cells will also allow their separation via flow cytometry and/or FACS analyis. Typical stains used in these assays will include, propidium iodide, Hoechst 33342, 7AAD and TO-PRO-3.

Stages of membrane change during apoptosis may be analyzed as well. Among these changes is the translocation of phosphatidylserine (PS) from the inner part of the cell membrane to the outside during the early to intermediate stages of apoptosis. Using FITC labeled Annexin V, one may be able to detect PS. Annexin V is a $Ca^{++}$ dependent phospholipid-binding protein. Again, dead cells will not bind Annexin V. Live cells are also negative for Annexin Binding. Apoptotic cells bind Annexin. One may combine this method of analyzing PS with the aforementioned method of using PI to stain DNA, thereby obtaining different profiles of live, dead, and/or apoptotic cells.

As mentioned above, a characteristic of apoptosis is the degradation of DNA. This degradation is usually carried out by activated Ca/Mg dependent endonucleases. Terminal deoxynucleotidyl transferase (TdT) will add biotinylated, BrdU or digoxygenin-labeled nucleotides to DNA strand breaks. Subsequent binding of the exogenously added streptavidin by the biotin, or a fluorochrome labeled anti-digoxygenin antibody may be used to then detect DNA degradation. This method allows one to correlate apoptosis with cell cycle status.

Another DNA binding dye that may be incorporated is the laser dye styryl-751 (LDS-751). Again, one may take advantage of the ability of apoptotic cells to exhibit different staining patterns than that of live or dead cells.

Laser capture micro-dissection (LCM) is a relatively new technology used for the procurement of pure cells from various tissues. Isolated tissues may be used to identify what effects a peptide may have on cells that have either internalized the peptide or have bound the peptide to an outer surface receptor. After transfer film is applied to the surface of a particular tissue section, one may activate a pulsed laser beam that, in turn, activates the film immediately above the cell(s) of interest (morphological changes are easily identified and cells may be selected on this basis). The film melts and fuses the underlying cells. The film can then be removed and the remaining cells, not contained within the film, are left behind. Once the cells are isolated, DNA, RNA or protein from the cells may then be purified. The isolation of the cells via LCM does not damage the cells because the laser energy is absorbed by the film. This particular technology may be useful in combination with any of the previously mentioned methods of detecting proteins using fluorescent molecules.

In vivo analyses using animal models are used to determine the effects of the peptide within an intact system. For example, in the field of immunology, peptides can be administered to an animal and its peripheral blood monocytes are used in the generation of antibodies directed against the peptide.

In the case of viral proteins—for use with, for example, viral vectors, therapeutic viruses, and viral capsid delivery compositions—desired characteristics to be retained can include the ability to assemble into a viral particle or capsid and the ability to infect or enter cells. Such characteristics are useful where the delivery properties of the viral proteins are of interest.

One application of the disclosed method is in the identification and development of peptides, and the oligonucleotides encoding those peptides, for use in subsequent gene replacement and/or gene enhancement therapy. For example, identifying anti-tumor peptides that specifically target the receptors involved in the metastatic spread of tumors. Target interacting peptides have been successfully isolated and identified using the minicell technology.

Invasion complexes have been shown to play a prominent role in cellular activities such as regulating actin and microfilament rearrangements within the target cell, and therefore playing critical role in pseudopod formation, as well as shutting down DNA synthesis and replication. The inhibition of DNA replication would then have a direct impact on apoptosis.

Invasion complexes also regulate normal and abnormal cell proliferation (for example, cancer cell metastasis and replication). Chemotaxis, migration and other modes of cellular recruitment and motility are also regulated by cellular interactions with invasion complexes. For example, egg fertilization may be inhibited or enhanced by such interactions.

Using the methods and materials described herein, one of skill in the art can isolate invasion complexes using proteins to which the complexes, normally or abnormally, bind as targets. For example, MCP-1, RAMF (a receptor for hyaluronic acid), glycosaminoglycans (GAG), and osteopontin (to isolate CD44 splice variants) may used to isolate whole or partial complexes. The isolated complexes can be used to screen for inhibitors of activity, using the minicell library technology described herein. Alternatively, peptides that bind to and either inhibit or enhance invasion complex activity may be identified using the disclosed mini-cell display technology.

The present invention will be further described below by way of the following non-limiting Examples and appended figures.

EXAMPLE 1

Construction of a 17K Antigen Fusion Plasmid for Minicell Display

A system was constructed to allow the controlled expression of oligonucleotide libraries genetically fused to the 17K antigen of *Rickettsia rickettsii*. The 17K antigen of *R. rickettsii*, when cloned into *E. coli* is displayed to the outer membrane. The N-terminal fragment, containing the lipid modification site, was assembled from the following primers and cloned into pZHA1.3, a plasmid derived from pUC19, by inserting the tac promoter upstream of the unique HindIII site.

Primers were dissolved in 10 mM Tris, pH 8.5, to a concentration of 100 nmol/µl. 10 µl of each was then mixed, heated to 80° C. for 5 min, cooled to 25° C. (ramp time 1 hour), and incubated at 25° C. for 1 hour. The annealed oligonucleotides were filled in with Klenow, and purified using a QIAquick PCR purification kit (Qiagen), before restriction digestion. The resulting double stranded DNA was cut with XbaI/BamHI and ligated overnight at 14° C. into the XbaI/BamHI of pZHA1.3 to form pZHA2.0.

The bold lower case bases of Primer 1 represent the Xba1 recognition site. The bold lower case bases of Primer 4 represent the BamHI recognition site. The bold upper case bases represent complementary bases used to generate double stranded sequences upon annealing. Primer 1 contains bases complementary only to Primer 2. Primer 2 contains bases complementary to Primer 1 and Primer 3. Primer 3 contains bases complementary to Primer 2 and Primer 4. Primer 4 contains bases complementary only to Primer 3.

```
Primer 1
                                          (SEQ ID NO:1)
tctagaATGAAACTTTTATCTAAAATTATGATTATAGCTCTTGCAAC
TTCTATGTTAGCCGCC

Primer 2
                                          (SEQ ID NO:2)
TCGGCGGACATTGCCAGGCCCGCCATACTTATTTGTTCCATGTC
CTTGTGAAGAACCGCCACGACCG

Primer 3
                                          (SEQ ID NO:3)
GGCGGTGCTGGCGGCGCATTACTTGGTTCTCAATTCGGTAAGG
GCAAAG

Primer 4
                                          (SEQ ID NO:4)
CCCGTTTCCTGTCGAACAACCTCATCCACATCCAGGTAATGAAC
CTCGTCAAGAACCACCTGTTTAGCCggatcc
```

The resulting plasmid, PZHA2.0 expresses the first 71 amino acids (SEQ ID NO:5) of the 17K antigen of *R. Rickettsii* (DNA encoding the first 71 amino acids is shown in SEQ ID NO:6), under the control of an IPTG inducible promoter (tac promoter). This vector was used for construction of the display library.

EXAMPLE 2

Construction of the Library

The primers were synthesized on an Applied Biosystems synthesizer (Forest City, Calif.).

1 mM of each primer was separately incubated in 100 µl of 10 mM Tris-HCl buffer, pH 8.0, containing 5 mM $MgCl_2$, 0.5 mM dNTPs and 5 U of Tac polymerase. Reactions were heated to 80° C. for 5 min, cooled to 25° C. (ramp time 1 h), and incubated at 40° C. for 15 min. This procedure was cycled 5 times. After the fifth cycle, 10 µl of each reaction mix was mixed pair-wise with 10 µl of samples from the other reaction as illustrated below. The total volume of each reaction was adjusted to 100 µl with Tris buffer, pH 8.0 containing 5 mM $MgCl_2$, 0.5 mM dNTP, and 5 U tac polymerase and cycled as described above. After the fifth cycle fresh 5 µl of 100 mM dNTP mix was added to each tube and the chaining reaction continued for another 10 cycles.

The reaction mixes from all 42 tubes (the original 6 primers and the 36 pair-wise tubes) were mixed (see table below) and double-stranded oligonuleotides, generated from the annealing of complementary regions, were purified as described above. The purified double stranded oligonucleotides were then incubated with 10 ug of pZHA2.0, previously digested with SmaI and tailed with dTTP and terminal transferase (to generate a 5' T overhang), and ligated overnight at 13° C.

Minicell *E. coli* strain DS410 was transformed with 5 µg of the resulting plasmid, pDIP1.0. The transformed bacteria were incubated over night in 10 ml of LB broth containing 200 µg/ml ampicillin. This culture represented the display library.

EXAMPLE 3

Purification and Labeling of Minicells

Plasmid pDIP1.0 was transformed into *E. coli* DS410. Transformed cells were grown in a 250-ml culture to stationary phase (the culture can be grown overnight but must have good aeration). Growing the cells in rich medium minimizes contamination of mini-cells by whole cells. The culture was spun down at 8200×g (7500 rpm in a Sorvall GSA rotor) for 20 minutes at 4° C. The cell pellet was resuspended in 5 ml of the supernatant. Resuspension was very thorough to prevent loss of minicells in the cell pellet during the sucrose gradient step. Pellet was resuspended completely by placing a magnetic stirring bar in the bottom of the centrifuge tube and mixing vigorously for 10 minutes at 4° C. The suspension was carefully layered on a 30-ml sucrose gradient (10–30%). The gradient was centrifuged in a cellulose nitrate ultracentrifuge at 4000×g for 20 minutes at 4° C. (e.g., in an SW27 rotor at 5500 rpm). After centrifugation, a thick, somewhat diffuse, white band of minicells was visible near the middle of the tube. Minicells were collected (the band) from the side with a 20 cc syringe. Minicells were removed from the sucrose solution by centrifugation at 20,000×g for 10 minutes at 4° C. (13,000 rpm in the Sorvall SS-34). The minicell pellet was resuspended in 1 ml of Methionine Assay Medium (Difco). The suspension was layered onto a 10-ml or a 30-ml sucrose gradient (10–30% gradient). The sucrose gradient was centrifuged at 4000×g for 20 minutes at 4° C. (e.g., in an SW40 rotor at 5700 rpm for a 10-ml gradient). The minicell band was removed as described above. Minicells were checked under the microscope for contamination. If any whole cells are observed within the microscope field, the minicells must be purified through another sucrose gradient. No contamination was observed and minicells were spun down as described above. Pellets were resuspended in 1 ml of Methionine Assay Medium. The optical density was read at 600 nm. If the minicells are to be used immediately, Assay Medium is added to give a concentration of $A_{600}$ 2.0/ml. If not, the minicells are spun 1–2 minutes in a microfuge and the pellet resuspended in enough Assay Medium containing 30% glycerol to give $O.D._{600}$=2. Store at −70° C. Minicells are generally active for at least 6 weeks.

EXAMPLE 4

Minicell Labeling and Induction of Expression

If the minicells to be labeled have been freshly prepared, they can be used directly (at a concentration of $O.D._{600}$=2). Minicells that have been previously frozen, first need to have the glycerol removed. In this case, the minicells are pelleted by centrifugation in a microfuge for 1–2 minutes. Minicell pellets are dissolved in enough Methionine Assay Medium to give $O.D._{600}$=2. For each sample to be labeled, 250 µl was placed into a microfuge tube. 5–10 µCi of $^{35}S$-methionine (alternatively, cold methionine may be used) was added to a volume of 1–2 µl, then 0.1 mM IPTG was added to induce the library. Cells were incubated at 37° for 90 minutes. Cells were chilled on ice and spun 1–1½ minutes in a microfuge. Supernatant was removed and discarded in the radioactive waste. Pellet was resuspended in 50–100 µl of 0.12M Tris, pH 7.1. Steps 5 and 6 were repeated two more times for a total of three washes. After the last wash, the pellet was resuspended in 20 µl 0.12 M Tris, pH 7.1.

EXAMPLE 5

Screening of Library for Bioactive Peptides

Several screening methods were utilized. Most of the methods follow a similar protocol outlined below.

a. Immunoprecipitate the target receptor b. Immobilize the receptor onto immuno-plates c. Incubate the plate with freshly isolated minicells d. Wash away unbound minicells e. Elute minicells from the plate and transform the plasmids isolated into fresh minicell strain DS410 for second cycle of screening. "Positive" clones selected are then constructed into a secondary library.

A tertiary library may be constructed from a third round of screening and those peptides selected may be used in functional screening assays to further isolate peptides of specific activity.

EXAMPLE 6

Amino Acid Analysis of Isolated Display Peptides

Minicells (2 $A_{600}$/ml) were resuspended in 1 ml 0.5 M formic acid (which cleaves between proline and glycine and releases the library from the display protein) then filtered through 1 KD cut off filtron NANOSEP™ filter to isolate peptides of greater than 1000 dalton MW. Samples were hydrolyzed under vacuum in 6 N HCl at 104° C. for 18 hours. The hydrolyzed samples were dried under vacuum and then reconstituted to 0.5 ml in amino acid analysis buffer. The samples were analyzed for amino acid content on a Beckman automatic amino acid analyzer using 0.2 M sodium citrate, pH 1.5 as the eluting buffer. The results (table 1, shown below) show that, as expected, amino acids were evenly distributed throughout the sample (ser, thr, trp, and met are unstable under these conditions and suffer extensive degradation).

TABLE 1

Amino acid analysis of display library.

| AA | AA MWt | nmol/ml | res/1000 | μg aa/ml | MRW Calc |
|---|---|---|---|---|---|
| Glu | 147.13 | 10.399 | 61.8203 | 91.530005 | 0.420176 |
| Gln | 146.15 | 0 | 0 | 0 | 0 |
| Asp | 133.1 | 11.64 | 69.1978 | 1.549284 | 0.519895 |
| Asn | 132.1 | 0 | 0 | 0 | 0 |
| Hyp | 131.3 | 0 | 0 | 0 | 0 |
| Leu | 131.17 | 9.565 | 56.8623 | 1.254641 | 0.433502 |
| Tyr | 181.19 | 7.948 | 47.2492 | 1.440098 | 0.260774 |
| Phe | 165.19 | 8.832 | 52.5046 | 1.458958 | 0.317845 |
| His | 155.16 | 12.714 | 75.5824 | 1.972704 | 0.487128 |
| Lys | 146.19 | 12.32 | 73.2407 | 1.801061 | 0.500995 |
| Trp | 204.22 | 0 | 0 | 0 | 0 |
| Arg | 174.2 | 10.468 | 62.2302 | 1.823526 | 0.357237 |
| HyLys | 162.19 | 0.703 | 4.17925 | 0.11402 | 0.025767 |
| Pro | 115.13 | 9.285 | 55.1977 | 1.068982 | 0.47944 |
| Thr | 119.12 | 5.261 | 31.2752 | 0.62669 | 0.262557 |
| Ser | 105.09 | 6.766 | 40.2221 | 0.711039 | 0.382746 |
| Gly | 75.07 | 10.7 | 63.6093 | 0.803249 | 0.84734 |
| Ala | 89.09 | 11.343 | 67.4326 | 1.010548 | 0.756902 |
| Cysl/2 | 121.15 | 11.571 | 68.7879 | 1.401827 | 0.56779 |
| Val | 117.15 | 8.673 | 51.5593 | 1.016042 | 0.440116 |
| Met | 149.21 | 6.405 | 38.0762 | 0.95569 | 0.255189 |
| ILe | 131.17 | 13.62 | 80.9687 | 1.786535 | 0.617281 |
| | Total nm/ml | 168.213 | 1000 | | 28.1433 |

Hyp=hydroxy-proline; HyLys=hydroxy-lysine; Cys1/2=Cystine

EXAMPLE 7

Peptide Screening by FACS Analysis

Blood is collected (roughly 75 microliters) into 1 ml PBS containing 5 μM EDTA and mixed immediately to prevent clotting. The tubes are kept on ice. The red blood cells are lysed using either Gey's solution or a buffered ammonium chloride (ACK) solution (or FACS lysis buffer, Bectin-Dickinson). Cells are washed two-three times with FACS buffer (PBS supplemented with either 1% BSA or 5% FBS and containing 0.05% $NaN_3$). The pellet is suspended from the final wash in roughly 50 microliters FACS buffer (or more if more than one analysis is to be done on a single sample). Roughly 50 microliters of cell suspension is added to 10 microliters of antibody solution and mixed gently. The proper concentration of antibody to use is determined prior to this step. The suspension is placed on ice for roughly 30 minutes. Cells are then washed two-three times with FACS buffer and suspended in 200–300 microliters of FACS buffer. Cells are incubated (at a ratio of roughly 1:100 cells:minicells) with FITC labeled minicells (in PBS at 2 O.D./ml) at room temperature for 15 minutes. (For live/dead discrimination, add roughly 10 microliters propidium iodide (PI) solution (stock solution, 10 μg/ml). If cells were to be fixed, PI was not added.

The cells are ready for analysis upon washing two-three times with FACS buffer and suspended in 200–300 microliters of FACS buffer.

The cells may be alive or fixed at the time of measurement, but are in monodispersed (single cell) suspension. They are passed single-file through a laser beam by continuous flow of a fine stream of the suspension. Each cell scatters some of the laser light, and also emits fluorescent light excited by the laser. The cytometer typically measures several parameters simultaneously for each cell (low angle forward scatter intensity-approximately proportional to cell diameter, orthogonal (90 degree) scatter instensity-approximately proportional to the quantity of granular structures within the cell, and fluorescence intensity at several wavelengths).

Light scatter alone is quite useful. It is commonly used to exclude dead cells, cell aggregates, and cell debris from the fluorescence data. It is sufficient to distinguish lymphocytes from monocytes from granulocytes in blood leukocyte samples.

The fluorescence intensity is typically measured at several different wavelengths simultaneously for each cell. Fluorescent probes are used to report the quantities of specific components of the cells. Fluorescent antibodies are often used to report the densities of specific surface receptors, and thus to distinguish subpopulations of differentiated cell types, including cells expressing a transgene. By making them fluorescent, the binding of display library to surface receptors can be measured. Intracellular components can also be reported by fluorescent probes, including total DNA/cell (allowing cell cycle analysis), analysis, newly synthesized DNA, specific nucleotide sequences in DNA or mRNA, filamentous actin, and any structure for which an antibody is available. Flow cytometry can also monitor rapid changes in intracellular free calcium, membrane potential, pH, or free fatty acids.

Flow cytometers involve fluidics, laser optics, electronic detectors, analog to digital converters, and computers. The optics deliver laser light focused to a beam a few cell diameters across. The fluidics hydrodynamically focus the cell stream to and within an uncertainty of a small fraction of a cell diameter, and, in sorters, break the tram into uniform-sized droplets to separate individual cells. The electronics quantify the faint flashes of scattered and fluorescent light, and, under computer control, electrically charge droplets containing cells of interest so that the cell can be deflected into a separate test tube or culture wells. The computer records data for thousands of cells per sample, and displays the data graphically.

EXAMPLE 8

Screening Display Library for Peptides that Bind to Stem Cells

Bone marrow from femurs and tibia of mice is prepared by methods familiar to one of ordinary skill in the art. The marrow is flushed and suspended in 5 mls staining media using a 23 gauge needle and filtered through nylon mesh into a 5 ml tube. The cells are pelleted by centrifugation (300×g) and resuspended in ACK hypotonic lysis solution (red blood cell lysis buffer—0.15 M NH4 Cl, 1 mM KHCO3, 0.1 mM Na2 EDTA, pH 7.3–100 μl/mouse), placed on ice for roughly 5 minutes and washed with 5 ml HBSS (or PBS plus 2% FCS) and spun. The solution is then resuspended in a "lineage cocktail" of appropriate antibody dilutions and buffer as determined by titration. This mixture is then incubated at 4° C. on a rotating platform for 30 minutes. To minimize non-specific binding of lineage antibodies, the mixture is washed and spun twice, firstly through a serum cushion (FCS). The resultant pellet is resuspended in roughly 3 ml of HBSS. DYNABEADS™ are added to a 1:1 bead/cell ratio (in 1 ml) and incubated at 4° C. on a rotating platform for 30 minutes.

At this point large rosettes of cells should be visible by eye following the DYNABEAD™ incubation. The mixture is brought to 5 ml with HBSS and placed on a magnet according to manufacturers specifications. Wash bound beads, spin, and transfer supernatents to new tube and spin again. Anti-rat IgG PE is added, incubated on ice for 20–30 minutes, and washed twice. A blocking solution of rat IgG is added (roughly 50 μl), and incubated on ice for roughly 15 minutes. A staining cocktail of Thy1.1, c-Kit, and Sca-1 is used to resuspend the mixture (use roughly 100 μl per mouse and antibody dilutions as determined by titration), and incubate at 4° C. for 30 minutes. The dead and dying cells are labeled with propidium iodide in staining medium (PI at 1 μg/ml).

This procedure will generally yield 2–5×$10^5$ bound peptides. (Average of 5000 stem cells/mouse).

EXAMPLE 9

Bioactive Peptides and Functions Derived from Minicell Display and Activity Assays The following is a table, Table 2, of bioactive peptides isolated and characterized, as described above.

TABLE 2

| PEPTIDE SEQUENCE | | FUNCTIONAL ACTIVITY |
|---|---|---|
| VLEP | (SEQ ID NO:7) | Inhibitor of macrophage recruitment by osteopontin, C5a, fibronectin |
| DDDRKWGFC | (SEQ ID NO:8) | Inhibits cell/collagen interaction |
| DQDQRWGYC | (SEQ ID NO:9) | Inhibits cell/collagen interaction |
| DRDRAWGYC | (SEQ ID NO:10) | Inhibits cell/collagen interaction |
| DRQWGLC | (SEQ ID NO:11) | Inhibits cell/collagen interaction |
| DADQKFGFC | (SEQ ID NO:12) | Inhibits cell/collagen interaction |
| ESHQKYGYCGGCDRNNP | (SEQ ID NO:13) | Inhibits cell/collagen interaction |
| DSVVYGLRSK | (SEQ ID NO:14) | Inhibits heparin binding |
| DSVAYGLKSK | (SEQ ID NO:15) | Inhibits heparin binding |
| DSVAYGLKSRSK | (SEQ ID NO:16) | Inhibits heparin binding |
| TPVVPTVDTYDGRGD | (SEQ ID NO:17) | Cell attachment/$alpha_v beta_x$ specific |
| TPFIPTESANDGRGDSVAW | (SEQ ID NO:18) | Cell attachment/$alpha_v beta_x$ specific |
| CVVVLVL | (SEQ ID NO:19) | Promotes cell entry of peptides |
| LDSAS | (SEQ ID NO:20) | Inhibits alpha4 integrin binding |
| LDSPPAALS | (SEQ ID NO:21) | Inhibits alpha4 integrin binding |
| AADVESPS | (SEQ ID NO:22) | Inhibits alpha4 integrin binding |
| WTGGDDSGSPSSPS | (SEQ ID NO:23) | Inhibits alpha4 integrin binding |
| SDV | (SEQ ID NO:24) | Inhibits alpha4 integrin binding |
| EPEESDVGGAADYP | (SEQ ID NO:25) | Inhibits alpha4 integrin binding |
| QESPSGTDLLVAGSSP | (SEQ ID NO:26) | Inhibits alpha4 integrin binding |
| TPVVPTVDTYDGRGDSLAY | (SEQ ID NO:27) | β integrin binding |
| DKKELAKFQAERSAAS | (SEQ ID NO:28) | $β_3$ attachment |

TABLE 2-continued

| PEPTIDE SEQUENCE | | FUNCTIONAL ACTIVITY |
|---|---|---|
| HDRKEFAKFEEEERARA | (SEQ ID NO:29) | $\beta_3$ attachment |
| HDRREFAKFQSERSRA | (SEQ ID NO:30) | $\beta_3$ attachment |
| HDRKEVAKFEAERSKA | (SEQ ID NO:31) | $\beta_3$ attachment |
| QSWKKQGSPSSPQRRSKGGRKP | (SEQ ID NO:32) | $\beta_3$ attachment |
| SDQDNNGKGSHES | (SEQ ID NO:33) | Endothelial cell attachment |
| SDQDQDGDGHQDS | (SEQ ID NO:34) | Endothelial cell attachment |
| GRGDNPS | (SEQ ID NO:35) | Fibronectin receptor binding collagenase induction |
| LVPSSKGRGDYLAQSQP | (SEQ ID NO:36) | Fibronectin receptor binding collagenase induction |
| PNGRGESLAY | (SEQ ID NO:37) | Inhibits fibroblast attachment, inhibits collagenase induction |
| DRYLKFRPV | (SEQ ID NO:38) | Inhibits melanoma cell attachment |
| HKFVHWKKPVLPSQNNQ | (SEQ ID NO:39) | Inhibits melanoma cell attachment |
| KGMNYTVR | (SEQ ID NO:40) | Inhibits, neutrophils, endothelium, fibrosarcomas melanoma attachment |
| DPGYIGSR | (SEQ ID NO:41) | Inhibits endothelial cell attachment |
| VLPTPTPPGYLSSRSSR | (SEQ ID NO:42) | Inhibits endothelial cell attachment |
| KNNQKSEPLIGRKKT | (SEQ ID NO:43) | Inhibits CD44 interaction with GAG |
| YYWRQQQKSDPVVSRRRSPS | (SEQ ID NO:44) | Inhibits CD44 interaction with GAG |
| ATWLPPR | (SEQ ID NO:45) | Anti-angiogenic |
| QVGLKPLV | (SEQ ID NO:46) | Anti-angiogenic |
| TPTVRGAAGSGNQN | (SEQ ID NO:47) | Anti-angiogenic |
| HGRFILPWWYAFSPS | (SEQ ID NO:48) | Inhibit homotypic aggregation of tumor cells |
| KKAKKSRRS | (SEQ ID NO:49) | Anti-adhesion (cell-cell) |
| KKGKKSKRS | (SEQ ID NO:50) | Anti-adhesion (cell-cell) |
| RRSRSSTGKKQKSSQSRKTA | (SEQ ID NO:51) | Anti-adhesion (cell-cell) |
| DGGRGDSLGWYRRGRGGARRSK AKKAAAKNNQKSEPLIGRKKT | (SEQ ID NO:52) | Apoptotic to tumor cells |
| KRSR | (SEQ ID NO:53) | Apoptotic to tumor cells |

It is understood that the disclosed invention is no limited to the particular methodology, protocols, and reagents described as these may vary. It is to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

I claim:

1. A method for identifying minicell hosts bound to a binding partner comprising:

(a) expressing a fusion protein in a minicell host comprising an outer membrane, wherein the fusion protein is encoded by a chimeric gene comprising: a DNA fragment encoding an N-terminal fragment of a 17K antigen of *Rickettsia rickettsii* consisting essentially of a signal sequence and lipid modification site which mediates localization of the fusion protein to the outer membrane, and a DNA fragment encoding a second peptide; (b) contacting the minicell host of step (a) with a binding partner; and (c) identifying the minicell hosts bound to the binding partner.

2. The method of claim 1 further comprising: (d) isolating the bound or unbound minicell host.

3. The method of claim 1, wherein the DNA fragment encoding the second peptide is from a DNA library.

4. The method of claim 1, wherein the binding partner is selected from the group consisting of carbohydrates, sugars, nucleic acid molecules, peptides, proteins, metals, inorganic molecules and synthetic drugs.

5. The method of claim 1, wherein the binding partner is selected from the group consisting of receptors, ligands, antibodies, vitamins, cofactors, enzymes, and neuromediators.

6. The method of claim 1 wherein the minicell host is a gram negative bacteria.

7. The method of claim 6 wherein the gram negative bacteria is selected from the group consisting of *E. coli, Salmonella typhimurium, S. anatum, S. enteritidis, S. pullorum, S. senftenberg, S. worthington, Vibrio cholera, Erwinia amylovora,* and *Haemophilus influenzae.*

8. The method of claim 1 wherein the minicell host is a gram positive bacteria.

9. The method of claim 8 wherein the gram positive bacteria is *Bacillus subtilis.*

10. The method of claim 1 further comprising: (d) isolating DNA from the gene encoding the fusion protein; and (e) subjecting the isolated DNA to analysis methods selected from the group consisting of determination of DNA base composition, determination of DNA base sequence, determination of molecular weight, and determination of secondary structures within the sequence.

11. The method of claim 1, wherein the DNA fragment encoding the N-terminal fragment of the 17K antigen comprises the first 213 nucleotides of the open reading frame of the 17K antigen of *Rickettsia rickettsii.*

12. The method of claim 1, wherein the expression of the fusion protein is controlled by an inducible promoter element.

13. The method of claim 12 wherein the inducible promoter element is selected from a group consisting of lac, tac, and trp.

14. The method of claim 1 further comprising: (d) cleaving the second peptide from the minicell host.

15. The method of claim 2 further comprising: (e) cleaving the second peptide from the minicell host.

16. The method of claim 15 further comprising: (f) isolating the peptide cleaved from the minicell host; and (g) subjecting the isolated peptide to methods selected from the group consisting of determination of amino acid composition, determination of amino acid sequence, determination of isoelectric point, and determination of molecular weight.

17. The method of claim 3, wherein the DNA fragment encoding the second peptide is at least three amino acids in length.

18. The method of claim 11 wherein the DNA fragment encoding the N-terminal fragment of the 17K antigen consists of the nucleic acid sequence of SEQ ID NO: 6.

19. The method of claim 1, wherein the N-terminal fragment of the 17K antigen comprises the first 71 amino acids of the 17K antigen.

20. The method of claim 19, wherein the N-terminal fragment of the 17K antigen consists of the amino acid sequence of SEQ ID NO: 5.

* * * * *